(12) United States Patent
Lucio Decanini et al.

(10) Patent No.: US 10,583,189 B2
(45) Date of Patent: Mar. 10, 2020

(54) EMULSIFIED VACCINE TO OBTAIN FORMULATIONS OF CONCENTRATED IGY IMMUNOGLOBULINS; PROCESSES AND USES FOR THE SAME

(71) Applicant: Investigación Aplicada, S.A. DE C.V., Tehuacán, Puebla (MX)

(72) Inventors: Eduardo Lucio Decanini, Puebla (MX); José Andrés Morales Garzon, Puebla (MX)

(73) Assignee: Investigacion Aplicada, S.A. DE C.V., Puebla (MX)

(*) Notice: Subject to any disclaimer, the term of this patent is extended or adjusted under 35 U.S.C. 154(b) by 0 days.

(21) Appl. No.: 15/505,379

(22) PCT Filed: Aug. 22, 2014

(86) PCT No.: PCT/IB2014/064028
§ 371 (c)(1),
(2) Date: Feb. 21, 2017

(87) PCT Pub. No.: WO2016/027135
PCT Pub. Date: Feb. 25, 2016

(65) Prior Publication Data
US 2017/0258899 A1    Sep. 14, 2017

(51) Int. Cl.
| | | |
|---|---|---|
| *A61K 39/39* | (2006.01) | |
| *A61K 39/395* | (2006.01) | |
| *A61K 39/42* | (2006.01) | |
| *A61K 39/12* | (2006.01) | |
| *A61K 39/15* | (2006.01) | |
| *A61K 39/215* | (2006.01) | |
| *C07K 16/02* | (2006.01) | |
| *C07K 16/08* | (2006.01) | |
| *C07K 16/10* | (2006.01) | |
| *C12N 7/00* | (2006.01) | |
| *A61K 39/00* | (2006.01) | |
| *A61K 39/002* | (2006.01) | |
| *A61K 39/108* | (2006.01) | |
| *A61K 39/112* | (2006.01) | |
| *A61K 39/08* | (2006.01) | |
| *A61K 39/102* | (2006.01) | |
| *C07K 16/12* | (2006.01) | |
| *C07K 16/44* | (2006.01) | |

(52) U.S. Cl.
CPC ......... *A61K 39/39* (2013.01); *A61K 39/0002* (2013.01); *A61K 39/002* (2013.01); *A61K 39/0258* (2013.01); *A61K 39/0275* (2013.01); *A61K 39/08* (2013.01); *A61K 39/102* (2013.01); *A61K 39/12* (2013.01); *A61K 39/15* (2013.01); *A61K 39/215* (2013.01); *C07K 16/02* (2013.01); *C07K 16/081* (2013.01); *C07K 16/10* (2013.01); *C07K 16/1242* (2013.01); *C07K 16/44* (2013.01); *C12N 7/00* (2013.01); *A61K 2039/54* (2013.01); *A61K 2039/552* (2013.01); *A61K 2039/55566* (2013.01); *A61K 2039/55583* (2013.01); *A61K 2039/575* (2013.01); *A61K 2039/70* (2013.01); *C07K 2317/11* (2013.01); *C07K 2317/76* (2013.01); *C12N 2710/18034* (2013.01); *C12N 2720/12334* (2013.01); *C12N 2770/10034* (2013.01); *C12N 2770/20034* (2013.01)

(58) Field of Classification Search
None
See application file for complete search history.

(56) References Cited

U.S. PATENT DOCUMENTS

| | | | |
|---|---|---|---|
| 4,357,272 A | 11/1982 | Polson | |
| 8,202,717 B2 * | 6/2012 | Zuckermann | C12N 7/00 424/204.1 |
| 2009/0238816 A1 | 9/2009 | Larsen | |
| 2011/0081374 A1 * | 4/2011 | Bublot | A61K 39/00 424/199.1 |

FOREIGN PATENT DOCUMENTS

| | | | |
|---|---|---|---|
| CN | 101428145 A | * | 5/2009 |
| CN | 102580083 A | * | 7/2012 |

OTHER PUBLICATIONS

Definition "EID50". http://www.fao.org/docrep/005/ac802e/ac802e0I.htm#bm21 retrieved Sep. 7, 2018.*
Bouvier et al. Viruses 2010, 2, 1530-1563.*
Marcol and Primol Medicinal White oils https://www.brenntag.com/norway/en/norway/media/news-detail-9-19586.jsp Retrieved May 15, 2019.*
Marcol search of the Trademark electronic search system (TESS) retrieved from tmsearch.uspto.gov/bin/showfield?f=doc&state=4801:vz2ua2.2.1 on May 15, 2019.*
"Marcol 82" Product Description http://www.ulei-mobil.ro/pdf/MobilIndustrieDataSheet/marcol_82.pdf retrieved May 16, 2019.*
International Search Report dated Jul. 24, 2015 based on co-pending International Application No. PCT/IB2014/064028, filed Aug. 22, 2014—8 Pages.
Written Opinion dated Jul. 24, 2015, based on co-pending International Application No. PCT/IB2014/064028, filed Aug. 22, 2014—10 Pages.
Pauly, Diana, et al., "IgY Technology: Extraction of Chicken Antibodies from Egg Yolk by Polyethylene Glycol (PEG) Precipitation", Journal of Visualized Experiments, May 2011, No. 51, pp. 1-6.
Yokoyama, Hideaki, et al., "A Two-Step Procedure for Purification of Hen Egg Yolk Immunoglobulin G: Utilization of Hydroxypropylmethylcellulose Phthalate and Synthetic Affinity Ligand Gel (Avid AL® )", Poultry Science, vol. 72, No. 2, 1993, pp. 275-281.
XP002738691—CN101428145, Beijing Cent Biology Co Ltd, May 13, 2009—Abstract Only.

* cited by examiner

*Primary Examiner* — Oluwatosin A Ogunbiyi
(74) *Attorney, Agent, or Firm* — McCarter & English, LLP (57) ABSTRACT

The present invention relates to a therapy for treating or preventing several diseases in animals, based on the administration of a highly concentrated avian derived immunoglobulins formulation, obtained from the egg yolk from hens previously hiper-immunized with a vaccine formulation comprising infectious agents or toxins antigens, a light mineral oil and a particulate adjuvant.

4 Claims, 6 Drawing Sheets
Specification includes a Sequence Listing.

EMULSIFIED VACCINE TO OBTAIN FORMULATIONS OF CONCENTRATED IGY IMMUNOGLOBULINS; PROCESSES AND USES FOR THE SAME

RELATED APPLICATIONS

This application is a national stage application filed under 35 USC 371 of PCT/IB2014/064028, filed Aug. 22, 2014, which is incorporated by reference herein in its entirety.

TECHNICAL FIELD OF THE INVENTION

The present invention relates to the field of veterinary medicine, particularly to the treatment of diseases in animals, and more specifically to the prevention or treatment of the Porcine Reproductive and Respiratory Syndrome (PRRS), the Porcine Epidemic Diarrhea (PED), the white spot syndrome in shrimps, bovine mastitis, the *Actinobacillus pleuropneumoniae* derived infections in porcins, coccidiosis in poultries and fungi toxin derived intoxications, by the administration of an avian derived immunoglobulins concentrated formulation, obtained from egg yolk from hens previously immunized with an emulsified vaccine formulation comprising antigens, a light mineral oil and a particulate adjuvant consisting of biodegradable polymer particles.

BACKGROUNDS

The health of the animals is the main key to obtain healthy and quality food. Thus, the control of the diseases and the use of all the available tools thereof is of outmost importance. Vaccination is one more of all the tools used daily in the farms, existing other tools as biosecurity measures so as to avoid the entrance of pathogens coming from other exploitations, the application of hygiene standards and the management of animals for reducing the dissemination of diseases among the animals of the same exploitation, strict feeding control, or the creation of a comfortable environment for the animals of the farm.

Notwithstanding, to date there are diseases which are not appropriately controlled. Among these diseases we find those produced by viruses, such as the one caused by the porcine reproductive and respiratory syndrome, which is a severe disease in the porcins, and which was reported in the United States in 1987 and later identified in many other European countries. In 1991, the isolation of the etiological agent was reported in Holland and was named as Lelystad virus, and due to the symptomatology observed in the pigs it was known as porcine respiratory and/or epidemic abortion.

Another viral disease which has not been controlled is the Porcine Epidemic Diarrhea (PED), which is a viral disease exclusive of the porcins, very contagious and in most of the cases it leads to death. This disease affects the digestive system and the suckling pigs die in a term of 3-5 days due to diarrhea and dehydration.

Another disease is the one caused by the white spot syndrome virus (WSSV), the main pathogen of the shrimp and responsible of great production and incomings losses in the farm industry worldwide. Up to day, there is no effective treatment for controlling the infection.

The treatment of the diseases caused by bovine *coronavirus* and *rotavirus* is also relevant.

Moreover, we find the diseases caused by bacteria, such as the bovine mastitis which produces inflammation of the mammary gland and its secreting tissues, thereby reducing the production of the milk volume and altering its composition, and even its flavor, besides increasing its normal bacterial load. According to its duration, it may be classified in acute or chronic disease. Regarding its clinical expression, it may be clinical or subclinical. This disease causes severe economic losses to the dairy industry.

We also find the diseases caused by *Actinobacillus pleuropneumoniae*, the bacteria responsible for respiratory disorders in porcins with worldwide distribution, being known 50 years ago, and having and increased occurrence since the 1980 decade, being frequent in feedlots. It is the main responsible for the porcine pleuropneumonia, as well as for the agent which is directly involved in the Porcine Respiratory Complex. This is a high-dissemination disease, highly contagious and in many cases lethal for porcins from the weaning to the sacrifice. It causes fibrinous pleuritis with very characteristic costal adherence in 30-50% of the porcins, and an increased mortality in acute events, with increased growing delay in the chronic events. Furthermore, it has been found that the *Actinobacillus pleuropneumoniae* is involved in the cases of otitis media, arthritis and osteomyelitis.

The treatment of the diseases caused by *E. coli, Salmonella* spp and *Clostridium perfringens* is also relevant for the health of the animals.

Furthermore, there is coccidiosis which is an infectious disease caused by strict intracellular life parasites of the *Eimeria* spp. and *Isospora* spp. genus. *Coccidias* are omnipresent as they exist in most of the cattle facilities worldwide. These parasites may infect a wide variety of animals including humans, poultry, ruminants, pigs, dogs, cats and other domestic animals, nevertheless in most of the cases, *coccidias* are specific species.

Additionally, other health problems faced by the cattle industry are those caused by trichothecenes which are toxins produced by several *Fusarium* fungi, particularly *Fusarium graminearum* and *Fusarium sporotrichioides*. They are produced in crops and they enter into the food through polluted ingredients. Trichothecenes are proven tissue irritants and its intake is mainly associated with oral injuries, dermatitis and intestinal irritation. The main physiological response to these mycotoxins is the loss of appetite. Thrichothecenes are strong suppressing mycotoxins affecting the immune cellular response with a direct impact over the marrow, spleen, lymphoid tissues, thymus and intestinal mucosa, where the actively divided cells are injured.

For the preventive control of all the above diseases, there are basically two forms of protection. They may be exposed to infectious agent-derived antigens for the stimulation of a protective immune reaction, or they may be administered with a preformed antibody obtained from an immune subject.

The first form of protection is achieved by vaccines which may be of different classes: live microorganisms, lyophilized, or dead in oily emulsions, and recently, the creation of cloned and recombinant vaccines. Each of them has advantages and disadvantages regarding protection, immune response and lasting of the protection. Nevertheless, it has been found that in some cases, there are undesired injuries in the host due to the vaccine virus (Tizard, I. R. 1998. *Vacunación y vacunas In: Inmunologia Veterinaria*. 5th. Edition, Mc. Graw-Hill. Pp. 285-305).

The second form of protection is also called passive immunity and involves the transmission of specific antibodies against infectious agents to a host.

Traditionally, at the research level, the antibodies are made mainly in mammals and less frequently in poultries.

The types of antibodies which are regularly made in mammals are monoclonal and polyclonal, and polyclonal in poultries (Larsson, et al., 1993. *Chicken antibodies: taking advantage of evolution. A review Poultry Sci.* 72: 1807-1812).

In the case of poultries, the *Gailus gallus domesticus* species (roosters and hens) is the only species from which the antibodies are obtained in a more accessible way and in a highly defined manner. The main serum antibody that is present in said species is lgG, although lgG is carried to the egg in a similar way to the transference of the mammal lgG through the placenta.

In the egg, immunoglobulin Y (IgY) is also present in a higher concentration in the egg yolk, nevertheless, there are also small amounts of IgY in the egg white. There has even been found that the amounts of IgY are higher in the egg yolk than in the hen serum (Larsson, et al 1993. *Chicken antibodies: taking advantage of evolution. A review Poultry Sc.* 72: 1807-1212).

In order to have an idea of the amount of antibodies produced by hens, it will suffice to note that a laying hen produces approximately 5 to 6 eggs per week with an approximate egg yolk volume of 15 ml, thus, within a week, a hen may produce egg yolk antibodies equivalent to 90 to 100 ml of serum or 180 to 200 of whole blood. This, when compared against the 20 ml of whole blood given by an immunized rabbit per week, allows us to clearly note the efficient productivity of the antibodies in egg yolk. Obviously, if bigger animals are used, such as horses or cows, the amount of serum and antibodies would be higher than in the egg, but this procedure is expensive and also more painful for the animals.

Among the advantages of the egg yolk antibodies, there are:
1. They do not bind the complement.
2. They do not bind to *Staphilococcus aureus* A Protein.
3. They do not react to the Rheumatoid factor.
4. Due to their philogenetics difference with mammal antibodies, IgY does not show crossed reaction with mammal antibodies.
5. Low production cost.

In the recent years, the egg yolk antibodies (immunoglobulins) have been used as diagnosis and therapy tools (Schmidt, et al. 1989). Thus, taking advantage of their philogenetics difference with mammal antibodies, Ig's have shown several advantages when used in immunodiagnosis. For example, egg yolk Ig's have been used for detecting several viruses by means of ELISA, immunodiffusion, immunofluorescence and complement fixation techniques. Due to their low isoelectric point as compared with the humans Ig, it has been used in electrophoresis assays for quantifying immunoglobulins in several animals serum (Altschuh, D. et al. 1984. *Determination of IgG and IgM levels in serum by Rocket Immunoelectrophoresis using yolk antibodies from immunized chickens. J. Immunolog. Methods.* 69:1-7; Larsson, A. et al. 1988. *Chicken antibodies: a tool to avoid false positive results by rheumatoid factor in latex fixation tests. J. Immunol. Methods.* 108:205-208; Larsson, A. et al. 1992. *Chicken antibodies: a tool to avoid interference by complement activation in ELISA. J. Immunol. Methods.* 156: 79-83; Larsson, et al 1993. *Chicken antibodies: taking advantage of evolution. A review Poultry Sci.* 72: 1807-1812; Schade, R. et al 1996. *The production of avian (Egg yolk) antibodies: IgY. Atla.* 24:925-934).

Regarding their therapeutic application, the IgY have been used as immunotherapy in different fields of science, for example, the oral administration of egg yolk immunoglobulins has prevented infections by rotavirus in mouse, bovines and porcins among others (Ikemori, Y. et al. 1992 *Protection of neonatal calves against fatal enteric colibacillosis by administration of egg yolk powder from hens immunized with 1<99-pillated enterotoxigenic Escherichia coli. Am. J. Vet. Res.* 53:2005-2008; Kuroki, M. et al 1994. *Passive protection against bovine rotavirus in calves by specific immunoglobulins from chicken egg yolk. Arch. Virol.* 138: 143-148; Marquart, R. 1998. *Antibody-loaded eggs for piglets: prevention of baby pigs from diarrhea. Proc. 2$^{nd}$ international Symposium on Egg Nutrition and Newly Emerging Ovo-Technologies.* Alberta, Canada).

Even the egg yolk IgY immunoglobulins have been used as antivenins against snakes and scorpions which may be injected for neutralizing the toxins with no risk of the common anaphylactic reactions found in the antivenins made in horse (Larsson, et al 1993. *Chicken antibodies: taking advantage of evolution. A review Poultry Sci.* 72: 1807-1812). Another application has been to prevent tooth decay in humans caused by *Streptococcus mutans* (Hatta, H. et al. 1997. *Passive immunization Against Dental Plaque Formation in Humans: Effect of a Mouth Rinse containing Egg Yolk Antibodies (IgY) Specific to Streptococcus mutans. Caries. Res.* 31:268-274).

In the case of the above mentioned animal diseases, several control and prevention measures have been developed through time due to the extension and economic impact of said diseases. Among the strategies for combating same we find the inactivated vaccines and the live virus vaccines. Nevertheless, none of these strategies has been 100% efficient.

In the specific case of the RNA viruses such as the PRRS virus or the PED virus, the lack of control is largely attributable to its high mutation index. This is a common feature among the RNA viruses arising from the lack of proofreading activity of the RNA polymerase. Thus, this failure along with the fast replication kinetics of the virus increase the risk of mutation and emergence of quasispecies (Manreetpal Singh Brar, Mang Shi, Raymond Kin-Hi Hui and Frederick Chi-Ching (2014) Leung mail Genomic Evolution of Porcine Reproductive and Respiratory Syndrome Virus (PRRSV) Isolates Revealed by Deep Sequencing. PLOS one). It has been reported that the genetic variation of the PRRS virus is between 0.48 and 1.32% (Murtaugh M., (2012) Use and interpretation of sequencing inf PRRSV control programs. Allen D. Leman Swaine Conference. Veterinary Continuing Education). These features of the PRRS virus explain the inappropriate protection obtained by vaccines.

One of the strategies used for preventing the diseases caused by these viruses are the autovaccines, which implies the development of vaccines not only by country, but by regions, on the contrary, the prevention by these means would not suffice.

There has also been observed that in the case of the virus causing PRRS, same is neutralized using immunoglobulins derived from the mammal serum (U.S. Pat. No. 5,489,805). These results teach that the immunoglobulins are an alternative for the treatment of ARN viruses. Nevertheless, the shortcoming with this alternative is that the antibodies thus obtained are unviable.

The application of immunoglobulins obtained from the egg yolk (IgY) has already been used in several applications of animal health and prophylaxis and also in humans. The researches performed by Akita and Nakai (Akita, E., Nakai, S. (2000). *Egg nutrition and biotechnology, CAB International*, New York, p. 301), show that the protective role of IgY against infectious agents is mainly attributed by its capacity of preventing the colonization of, or neutralizing the toxins.

Therefore, an object of the present invention refers to the obtention of avian derived concentrated IgY immunoglobulins formulations, which are effective and safe against several agents that infect animals, including, for example, the PRRS virus, the Porcine Epidemic Diarrhea (PED) virus, the White Spot Syndrome Baculovirus Complex, bacteria causing bovine mastitis, *Actinobacillus pleuropneumoniae* and coccidiosis, as well as the intoxications caused by trichothecenes, as its feasibility could directly influence towards an important decrease in the expenses associated with vaccination processes and more importantly, would highly reduce the productive losses associated with said diseases.

SUMMARY OF THE INVENTION

In order to achieve the objects of the present invention, the capacity of a formulation comprising concentrated IgY immunoglobulins specific for neutralizing the PRRS virus, obtained from egg yolks from hens previously immunized with an emulsified vaccine formulation comprising antigens derived from one or more PRRS virus strains, light mineral oil and a particulate adjuvant consisting of biodegradable polymer particles, micro-particles or nano-particles, was experimentally assessed.

The inventors of the present application have successfully achieved the objects of the invention and have surprisingly found that with the antigens of one or more different strains of the PRRS virus, carefully selected, the expected crossed protection against other strains of the same virus may be produced, as well as the induction of immunoglobulins production which are capable of neutralizing a higher number of PRRS viruses circulating in the field. Further, the emulsified vaccine formulation must include a light mineral oil, for example MARCOL, and a particulate adjuvant consisting of biodegradable polymer particles, micro-particles or nano-particles so as to enhance the vaccination, preferably using a lineal polysaccharide comprised of randomly distributed chains of β-(1-4)D-glucosamine (deacetylated units) and N-acetyl-D-glucosamine (acetylated units), such as Chitosan.

With such prepared emulsified vaccine formulation, the laying poultries are immunized for obtaining, through the egg yolk, IgY immunoglobulins neutralizing against infectious agents or toxins, which, after an extraction, delipidation and concentration method, where minimal amounts are used, one finally obtains a concentrated formulation of said IgY immunoglobulins capable of achieving an unexpected protection of up to approximately 100%, besides regularizing the S/P level in infected farms.

The invention has the additional advantage of stabilizing the herd, flock or passel, thus reducing the circulation of the infectious agents. Also, the used of the avian origin concentrated formulation of the invention as a schedule, the generation of maternity subpopulations is reduced, and the seroconversion of the fattening animals is delayed at the weaning.

To date, the assessed immunoglobulins have been mammal serum derived, and they have only been tested in an experimental model challenged with the same virus strain with which they were vaccinated. This means, unlike the present invention, the vaccines of the prior art have been only tested for the homologue protection (WO 02/067985).

Further, the avian derived concentrated formulation of the invention, comprising concentrated IgY immunoglobulins, may be used in any reproductive stage of the animals without there being side or undesirable effects.

The avian derived concentrated formulation of the invention is highly concentrated and protects against higher challenges of the infectious agent or toxins. There are pieces of evidence against challenges of 10 to the seventh (10,000,000), which is far higher than that already known in the prior art (WO 2007/061281 A2).

Additionally, with the processes of the present invention, the concentration of the immunoglobulins (IgY) neutralizing against the infectious agents circulating in the field, or toxins, is achieved, in such a way that a concentrated wherein only 1 ml or 3 ml per dose is applied, while the application of the vaccines and the products of the prior art, is up to 5 ml and even more up to 10 ml, and even more than 10 ml (WO 2007/061281 A2).

The decrease in the volume of application is beneficial in several aspects. First because the application is eased, second because the production costs are reduced and third because the transportation to different areas uses less space.

The doses of 1 ml or up to 3 ml that may be achieved thanks to the concentrated immunoglobulins (IgY) formulation of the present invention, depending obviously on the severity, follow an immunization schedule and even when they are not a vaccine per se, they may work as such and control the infected animals. The avian derived concentrated formulation of the invention falls within the passive immunity scope as it contains immoglobulins neutralizing against infectious agents or toxins.

BRIEF DESCRIPTION OF THE DRAWINGS

These results indicate that the IgY antibodies titers produced by the vaccine containing six PRRS virus strains, and using a formulation with MARCOL mineral oil and chitosan, is the one that induces the highest amount of antibodies against the Porcine Reproductive and Respiratory Syndrome.

FIG. 2 shows the IgY antibodies mean titer in the yolk using three kinds of vaccine formulations. Group A was vaccinated with 2 vaccines made with mineral oil, each of them containing 3 PRRS virus strains and applied alternatively and in a monthly base. Group B was vaccinated with 1 vaccine made with mineral oil and chitosan, which contains 6 different strains of the PRRS virus and was applied monthly. Group C was vaccinated with a vaccine made with MARCOL mineral oil and chitosan, which contains 6 different strains of the PRRS virus and was applied monthly.

FIG. 3 shows the increase in the immunoglobulins titer after applying the concentration process. Yolk immunoglobulins were extracted, one part was quantified by the MNT method and the rest underwent the concentration process. Group A was vaccinated with 2 vaccines made with mineral oil, each containing 3 PRRS virus strains and applied alternatively in a monthly base. Group B was vaccinated with 1 vaccine made with mineral oil and chitosan, containing 6 different strains of the PRRS virus and was applied monthly. Group C was vaccinated with a vaccine made with MARCOL mineral oil and chitosan, containing 5 different strains of the PRRS virus and applied monthly.

FIG. 5 shows the monitoring of mortality from week 3 through 26. The groups that were treated with the avian derived IgY immunoglobulins concentrated formulation of the invention are highlighted in a more intense blue box (groups 7 to 16).

DETAILED DESCRIPTION

Laying Poultries Immunization for the Obtention of Immunoglobulins (IgY) Neutralizing Against Infectious Agents or Toxins An emulsified vaccine comprised by antigens for producing neutralizing antibodies and not only against a single strain of a determined infectious agent or toxin, but against several strains circulating in the field (epidemiological surveillance) or toxins is produced.

The above is relevant for the ARN viruses case, as from our research we noted that not all the strains of a circulating virus may be neutralized with antibodies produced from the antigens of an specific strain. The same happens with the vaccines against virus, as when the vaccination occurs with a heterologous strain, the protection is partial.

In the case of microorganisms, the strains were selected by crossed MNT (microneutralization) tests. This test consists in testing the neutralization level of the immunoglobulins, obtained using a vaccines with defined strains, against the new isolation of the infectious agent. In our work in the lab, we have determined that if the new isolation has titers lower than 1:160 in the MNT, then said strain is considered as a candidate to be included in a new vaccine. Thus, to date our vaccine has contained some strains conferring a wide neutralization spectrum against the strains of the infectious agents circulating in Mexico. Nevertheless, this does not limits the invention and it must not be understood that the invention refers to a vaccine including only the selected strains, as the strains of the infectious agent may vary as the circulation in field of the new strains is being monitored, which may be included lately in the vaccine for maintaining the protection in the animals. The neutralization spectrum of the present invention could also be widened and suited against other strains of infectious agents circulating in other countries or in other regions.

The strains of the infectious agent may be field isolations obtained from sick animal's serum or tissue. The base for the selection, as above cited, lays on the cross microneutralization test between the different isolated strains with the Ig's contained in the product and produced from the selected strains.

In the case of the PRRS virus, the cellular line MARC-145 may be replicated and not more than five passes of the working seed are performed, so as to avoid attenuation. The selected antigens are inactivated with 0.01% formalin or by any other method described in the prior art. In our lab, we have determined that the antigens mixture must have each one a minimum $DIE_{50\%}$ $10^4$/ml titer.

Considering the above, the emulsified vaccine formulation for immunizing poultries further comprises antigens from one or more carefully selected strains, a light mineral oil and particulate adjuvant consisting of a biodegradable polymer particles, micro-particles or nano-particles so as to enhance the vaccination, particularly, a lineal polysaccharide comprised of randomly distributed chains of $\beta$-(1-4)D-glucosamine (deacetylated units) and N-acetyl-D-glucosamine (acetylated units), such as Chitosan, is preferred.

The formulation of the water in oil type vaccination may comprise around 50% to 70% and preferably around 60% to 67% of MARCOL mineral oil, around 20% to 40% and preferably around 28% to 35% of water with PRRS virus antigens; around 5% to 15% of each strain of the PRRS virus selected based on the above explained criteria, around 2% to 5% of polyoxyethilene monooleate Sorbitan (Tween 80), around 2% to 8% of Sorbitan monooleate Sorbitan (Span 80) and an adjuvant such as a lineal polysaccharide comprised of randomly distributed chains of $\beta$-(1-4)D-glucosamine (deacetylated units) and N-acetyl-D-glucosamine (acetylated units), particularly 4% to 6% of chitosan. For preparing the vaccination, each component is added one by one under a stirring system during 1 to 5 minutes, the chitosan being added at the end.

The vaccine is applied to the pathogen-free laying poultries, 0.5 ml, once a month, subcutaneously starting on week 8 and until week 60 of age, so as to finally obtain a formulation of immunoglobulins (IgY) neutralizing of the infectious agents or toxins from the egg yolk.

Particularly, the antibodies level for each of the strains of the infectious agent is assessed by the microneutralization (MNT) of the egg yolks samples collected from the vaccinated flock. The minimum serum titer must comply with the 1:160 criteria.

After immunization, the eggs are collected from the immunized poultries and undergo an extraction, delipidation and immunoglobulins concentration process from the egg yolk.

Extraction, Delipidation and Immunoglobulins IgY Concentration Process

The following steps are performed for the extraction and concentration of immunoglobulins IgY neutralizing of infectious agents or toxins from the egg yolk.

The egg yolk is diluted 1:4 or 1:8 (without the egg white) with 0.01% sodium azide and is stored under refrigeration during at least all day, preferably from 12 to 24 hours. Then, the supernatant is separated and 1 to 15% hydroxypropyl-methylcellulose phtalate (HPMCP) is added in a ratio of 0.25 ml per each 100 ml of water. It is allowed to rest for at least 24 hours. The lipids layer formed in the upper part of the solution is separated and the aqueous part is filtered, then PEG is added, preferably 8000, in a 5-30% W/V ratio, mixed and allowed to rest during at least 4 hours, but preferably it is allowed to rest over night at 4° C. Then, it is centrifuged during 20 to 30 minutes and the supernatant removed. The resulting tablet is solubilized with PBS 1× or TRIS buffer, at a volume equivalent to 10% of the original volume.

Therapies with the Concentrated IgY Immunoglobulins Formulation of the Invention The formulation resulting from the extraction, delipidation and concentration process of the IgY immunoglobulins neutralizing of infectious agents or toxins, obtained from the egg yolk of hens previously immunized with an emulsified vaccine comprising antigens, a light mineral oil and a particulate adjuvant consisting of biodegradable polymer particles, such as a lineal polysaccharide comprised of randomly distributed chains of β-(1-4)D-glucosamine (deacetylated units) and N-acetyl-D-glucosamine (acetylated units), (chitosan), may comprise: around 0.8% o 5% of concentrated IgY immunoglobulins against pathogens or toxins of the invention, preferably around 1% of concentrated immunoglobulins, around 80% to 90% of water and around 0.001% to 0.03% of preservatives. The treatment dose of the concentrated formulation of the invention may be of 1 ml and of 3 ml at most, which achieves the neutralization of the field varieties of the infectious agents or toxins of the invention, unexpectedly providing a protection of up to 100% in animals, besides regularizing the S/P level in infected farms, as shown below.

Considering the above, in a first embodiment, the present invention refers to an emulsified vaccine formulation comprising antigens, a light mineral oil, preferably MARCOL mineral oil, and a particulate adjuvant consisting of biodegradable polymer particles, such as a lineal polysaccharide comprised of randomly distributed chains of β-(1-4)D-glucosamine (deacetylated units) and N-acetyl-D-glucosamine (acetylated units), preferably Chitosan. Further, the vaccine formulation of the present invention comprises one or more emulsifiers, such as polyoxyethilene monooleate Sorbitan (Tween 80), Sorbitan monooleate Sorbitan (Span 80), or a mixture thereof.

The antigens may come from one or more different strains from one or more infectious agents or toxins, such as for example viruses, bacteria or protozoa, more particularly from the PRRS virus, the PED virus, the White Spot Syndrome Baculovirus Complex virus, *Rotavirus* spp. or *Coronavirus* spp., and more particularly from the PRRS viruses having a nucleotide sequence of the ORF5 gen selected from the group consisting of SEQ. ID. NO:1, SEQ. ID. NO: 2, SEQ. ID. NO: 3, SEQ. ID. NO: 4, SEQ. ID. NO: 5, SEQ. ID. NO: 6 and SEQ. ID. NO: 7, and also from the Porcine Epidemic Diarrhea (PED) virus. Also, the antigens may come from one or more bacteria, such as *Salmonella* spp., from the selected ones from the group consisting of: *Staphylococcus aureus, Streptococcus agalactiae, Escherichia coli, Corynebacterium pyogenes* and *Mycoplasma bovis*, or also from *Actinobacillus pleuropneumoniae*. The antigens may further come from one or more protozoan selected from the group consisting of: *Eimeria tenella, Eimeria acervuiina* and *Eimeria maxima*, or from toxins produced by fungi, such as thricothecenes and more particularly from 4-deoxynivalenol (DON). Moreover, the antigens may come from one or more different strains of one or more viruses, one or more bacteria, or one or more protozoan, such as for example from antigens derived from *Eschericihia coli, Salmonella* spp., *Clostridium perfringens, Rotavirus* spp. and *Coronavirus* spp. Particularly, the antigens may also come from the group consisting of *Escherichia coil, Rotavirus* spp. and *Coronavirus* spp.

The emulsified vaccine formulation of the invention may contain viral strains selected by having a serum titer lower than 1:160, assessed by crossed microneutralization using an immunoglobulins pool obtained with the current vaccine.

Likewise, the emulsified vaccine formulation of the invention may contain an antigens mixture with titers higher than $DIE_{50\%}$ $10^4$/ml.

According to the selected antigen or antigens, the present invention also refers to the use of the emulsified vaccine formulation in preparing a concentrated IgY immunoglobulins formulation composition useful for the treatment of the Porcine Reproductive and Respiratory Syndrome (PRRS), the treatment of the Porcine Epidemic Diarrhea (PED), the treatment of the white spot syndrome in shrimps, the treatment of bovine mastitis, the treatment of infections produced by *Actinobacillus pleuropneumoniae* in porcins, the treatment of coccidiosis in poultry, the treatment of intoxications caused by trycothecenes, particularly wherein the trycothecene is 4-deoxynivalenol (DON), respectively, wherein the emulsified vaccine formulation is subcutaneously administrable to the laying poultries.

In another embodiment, the present invention refers to a process for the extraction and concentration of immunoglobulins from egg yolk of hens previously immunized with the vaccine formulation of the present invention, characterized by the following steps:

a) The yolk is diluted 1:4 or 1:8 (without the egg white) with 0.01% sodium azide and stored under refrigeration during at least 24 hours.

b) The supernatant is separated and hydroxypropyl methylcellulose phtalate (HPMCP) is added at 1-15% in a 0.25 ml per each 100 ml of yolk ratio. It is allowed to rest during at least 24 hours.

c) The lipid layer formed in the upper part is separated from the solution and the aqueous part is filtrated.

d) PEG is added, preferably PET 8000, in a 5-30% W/V ratio, mixed and allowed to rest during at least 4 to 12 hours at 4° C.

e) It is centrifuged during 20 to 30 minutes and the supernatant is removed.

f) The resulting tablet is solubilized with PBS 1× or TRIS buffer, at a volume equivalent to 10% of the original volume, maintain pH at 7.

In an additional embodiment, the present invention is aimed to an avian derived concentrated IgY immunoglobulins formulation obtained by the extraction, delipidation and immunoglobulins concentration from egg yolk derived from hens previously hiper-immunized with the emulsified vaccine of the invention. Said avian derived concentrated formulation of the invention may further comprise around 70% to 85% of water and/or around 0.001% to 0.03% of preservatives. Particularly, the concentrated IgY immunoglobulins formulation is characterized in because it comprises 0.8% to 5% of concentrated IgY immunoglobulins neutralizing the virus causing PRRS.

Further, depending on the selected antigen or antigens, the present invention also refers to the use of the avian derived concentrated IgY immunoglobulins formulation of the invention in preparing a medicament for treating the Porcine Reproductive and Respiratory Syndrome (PRRS), the Porcine Epidemic Diarrhea (PED), the white spot syndrome in shrimps, bovine mastitis, infections produced by *Actinobacillus pleuropneumoniae* in porcins, coccidiosis in poultry, intoxications caused by trycothecenes, particularly wherein the ones caused by trycothecenes such as 4-deoxynivalenol (DON), wherein the medicament may be parenterally administered, preferably intramuscularly administered, or orally administered and with food, as applicable.

The following examples show the results of the application of the concentrated formulation of the invention in porcins. Nevertheless, said examples are provided merely as illustration and are not to be considered as limitations.

Example 1

Two vaccines, each containing three strains of the PRRS virus, were prepared, using a formulation without MARCOL mineral oil and chitosan. These vaccines were applied monthly and in an alternate way to the poultries; this means, one vaccine was administered one month and the other one the next month, and so on.

After the immunization, the eggs from the immunized poultries were collected and underwent an immunoglobulin extraction process from the egg yolk, as above described.

As a result of the above immunization, a formulation with IgY immunoglobulins neutralizing of the PRRS virus was obtained, but with a low concentration.

Figure 1:
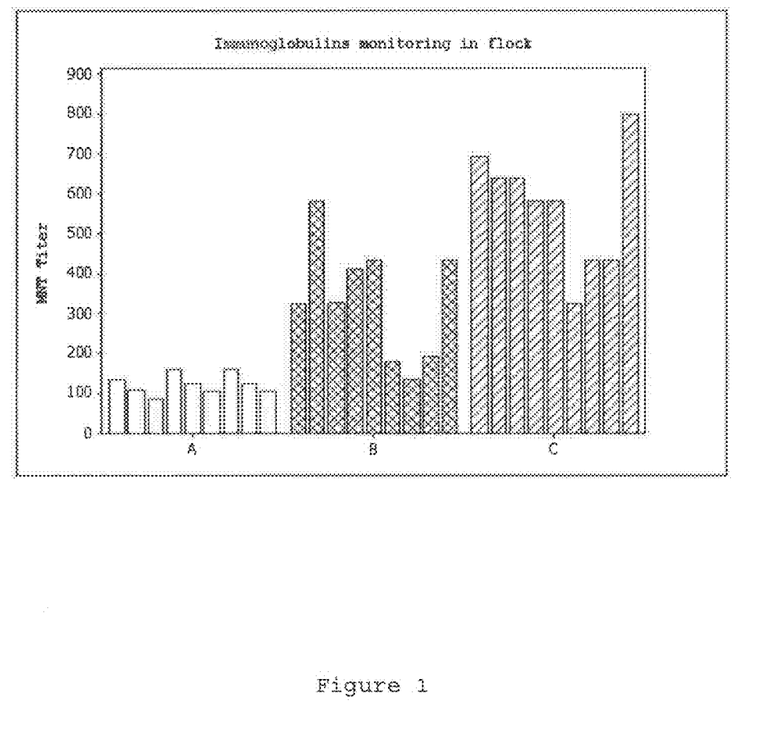
FIG. 1 shows the MNT titration results of different samples of egg collected from poultries immunized with different vaccines. Group A was vaccinated with 2 vaccines made with mineral oil, each containing 3 PRRS virus strains and applied alternatively in a monthly base. Group B was vaccinated with 1 vaccine made with mineral oil and chitosan, which contains 6 different strains of the PRRS virus and applied monthly. Group C was vaccinated with a vaccine made with MARCOL mineral oil and chitosan, containing 6 different strains of the PRRS virus and applied monthly.

FIG. 1 shows the results of this experiment (group A), wherein the low performance of the IgY immunoglobulins neutralizing the PRRS virus of the previously obtained formulation may be noted, which is incapable of carrying an efficient treatment in porcins suffering the Porcine Reproductive and Respiratory Syndrome, as the use of volumes higher than 5 mL and which protect $10^4$ titers is necessary. Further, this experiment was complicated and troublesome due to the handling of two vaccines.

Example 2

One vaccine containing six different strains of the PRRS virus was prepared, using a formulation without MARCOL mineral oil and chitosan, which was administered to the poultries in a monthly immunization schedule.

After the immunization, the eggs from the immunized poultries were collected and underwent an immunoglobulin extraction process from the egg yolk, as above described.

As a result of the above immunization, the performance as compared to the experiment of Example 1 was improved, but did not suffice (See FIG. 1, group B).

As a result of this experiment, we learned that the IgY immunoglobulins neutralizing the PRRS virus performance is inappropriate for carrying out an effective treatment in porcins suffering the Reproductive and Respiratory Syndrome.

Example 3

Again, one vaccine was formulated, but now using MARCOL mineral oil as the light mineral oil and chitosan as the particulate adjuvant. This time, antigens of 6 strains of the PRRS virus were included in one single vaccine.

After the immunization, the eggs from the immunized poultries were collected and underwent an immunoglobulin extraction process from the egg yolk, as above described.

Figure 2:
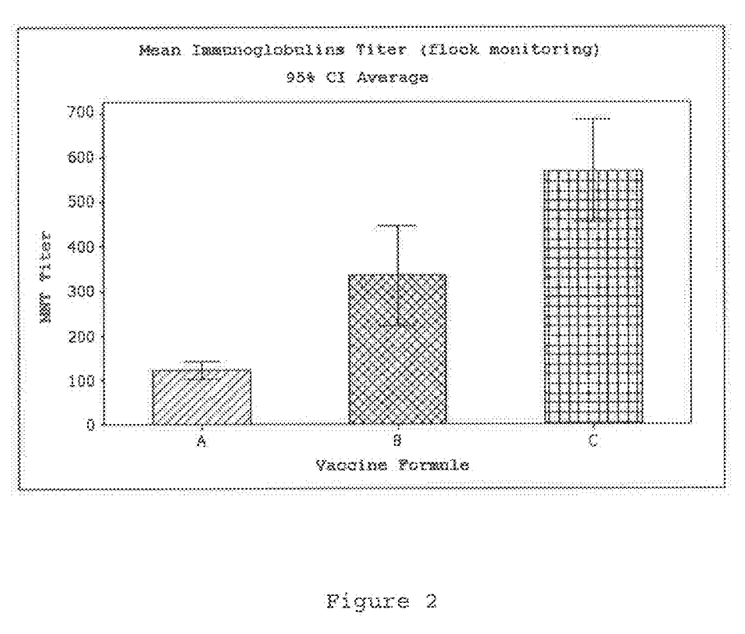

Our results indicate that the antibodies titers increase up to 2 fold regarding that obtained with the formulation of the experiment in Example 2 (see FIG. 2, group C).

FIGS. 1 and 2 show the results of this experiment, wherein it may be noted that the performance of the IgY immunoglobulins neutralizing of the PRRS virus relevantly increases when a formulation with MARCOL mineral oil and chitosan is used, which is appropriate for carrying on an effective treatment in porcins suffering of the Reproductive and Respiratory Syndrome.

Example 4

In this example, the immunoglobulins finished product was analyzed. Laying poultries were immunized, the eggs of the immunized poultries were collected and the egg yolks underwent an extraction and immunoglobulins concentration process, as above described. The vaccines used to immunize the flocks were the same used in the Examples 1 to 3, but in this case, the size of the batch was increased to 10,000 eggs per flock.

Figure 3:
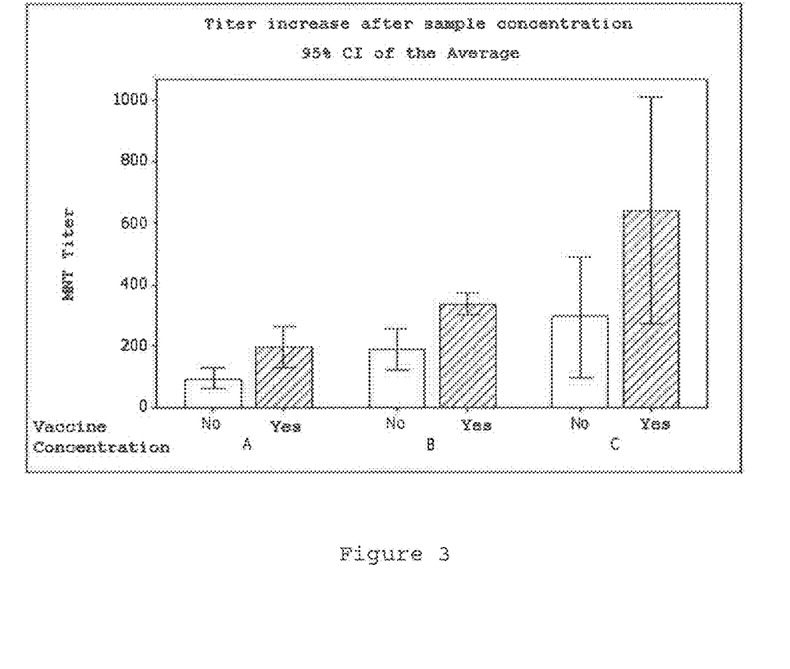

Our results indicate that the above described concentration process increases the antibodies titers regarding that obtained without said process. The concentration increase goes from 1.6 to 2.1 fold (FIG. 3). As a result of this experiment, we found that the performance of IgY immunoglobulins neutralizing the PRRS virus is appropriate for carrying on an effective treatment in porcins suffering the Reproductive and Respiratory Syndrome, using a lower volume to reach the protection.

Example 5

Immunoglobulins (IgY Type) Application in the Females of the Reproductive Herd

A longitudinal monitoring of the presence of antibodies against the PRRS virus was performed by assessing the sera of 30 randomly selected sows from a full exploitation cycle farm with 500 sows, located in Western Mexico. This farm produces suckling pigs which are negative to PRRS virus, and which pollute through their productive life.

The reproductive herd was treated with a 1 ml application of the avian derived concentrated IgY immunoglobulins formulation of the invention, intramuscularly, each 4 months and one repetition within 15 days. Then, weekly applications were made at days 70 and 85 of the gestation.

The broodstock sows were bimonthly monitored so as to determine the viral movement. Blood samples were taken from the same 30 animals initially selected. For assessment, ELISA technique was used (IDEXX, PRRS X3), which is an indirect way to measure the effectiveness of the treatment with concentrated IgY. The kit measures the levels of IgG type antibodies produced by the pig in response to a viremia. Thus, if the pig is infected, it will produce IgG type antibodies as a response and S/P values higher than the cut-off point will be obtained, but if there is no viremia, the kit will yield S/P values lower than the cut-off point. The cut-off point of ELISA was 0.4 S/P.

Figure 4:
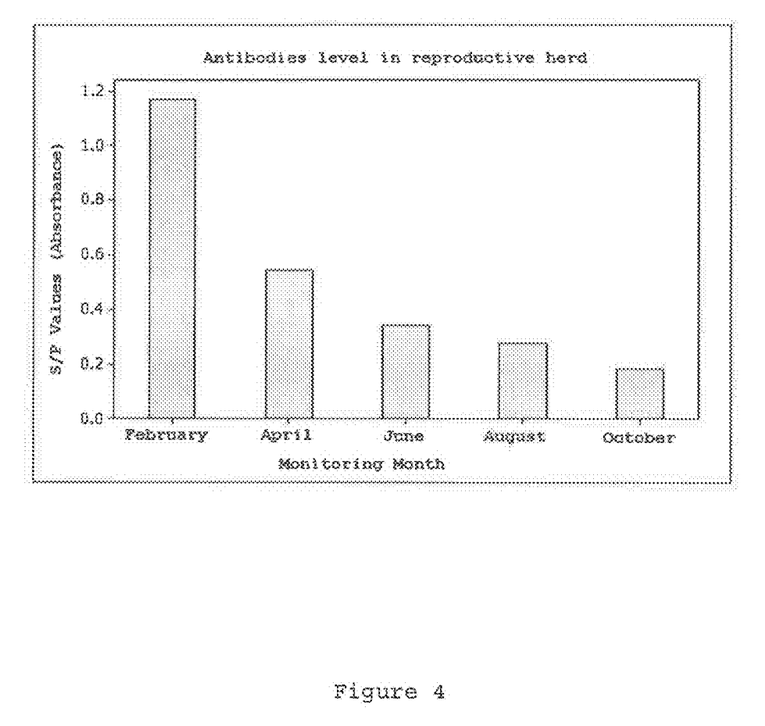
FIG. 4 shows the gradual decrease of the antibodies levels in the females of the reproductive herd after receiving the concentrated formulation.
Figure 5:
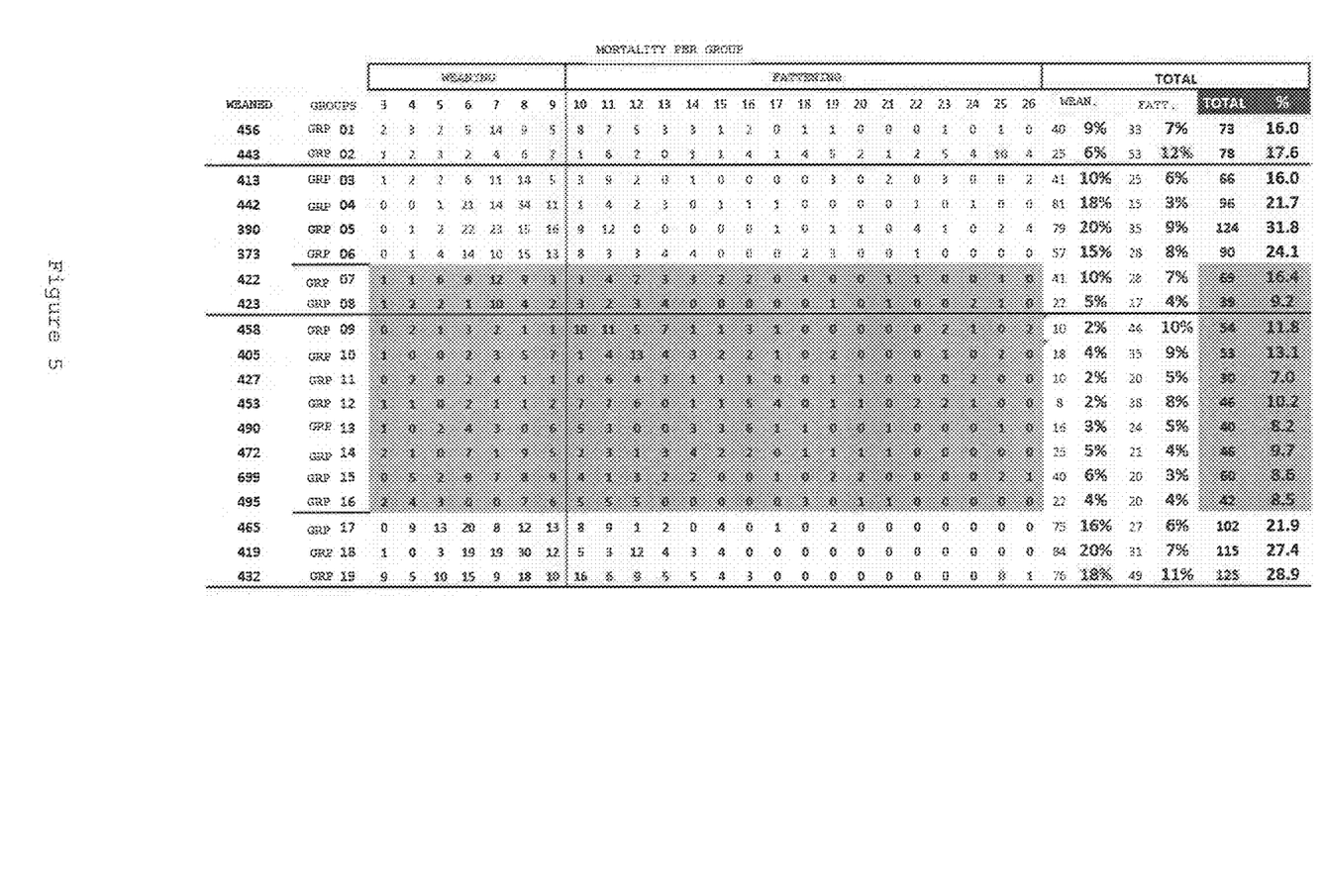
Figure 6:
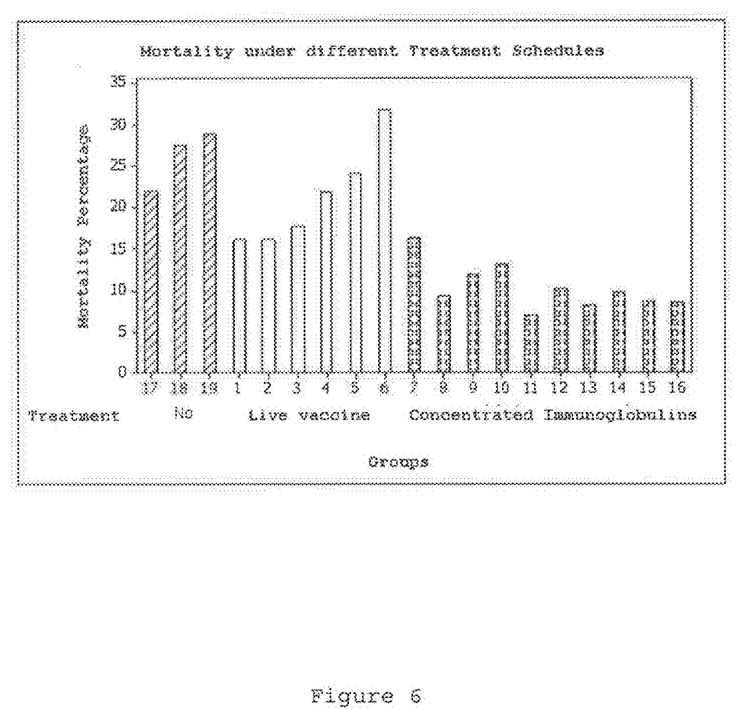
FIG. 6 shows a chart with the mortality percentages of each assessed group, wherein those that were treated with the avian derived concentrated formulation of the invention are highlighted.

FIG. 4 shows that the treatment applied to the herd gradually reduces the antibodies levels as the bimonthly monitoring is being performed and thus, it is shown that the PRRS virus has been neutralized by the applied immunoglobulins (IgY type), thereby limiting the infection. It is worth to note that, surprisingly, our product neutralized the virus in such a way that after 6 months there was no record of a PRRS virus reinfection. This is shown as a substantial difference between the productive parameters of negative and positive farms was recorded.

Example 6

Concentrated Immunoglobulins (IgY) Application in Suckling Pigs

The assessment results of the viremia decrease in the PRRS virus clinically affected suckling pigs are shown in this example. The suckling pigs did not show viremia during the maternity stage (first 3 weeks). Nevertheless, there was clinical evidence of viremia around 6-8 weeks of age. This was proved by the PCR technique in real time, wherein 5 pools of viremic animal sera were generated; each pool comprised by sera of 5 different porcins (a total of 25 porcins assessed). As it is shown in the table, the viral load reached titers between $6.16 \times 10^5$ and $2.24 \times 10^7$.

| Identification | Initial Viral Load | Viral Load After Treatment |
|---|---|---|
| Weaning 6 | $6.16 \times 10^5$ | NEGATIVE |
| Weaning 6 | $4.98 \times 10^6$ | NEGATIVE |
| Weaning 7-8 | $5.54 \times 10^4$ | NEGATIVE |
| Weaning 7-8 | $2.24 \times 10^7$ | NEGATIVE |
| Weaning 7-8 | $1.21 \times 10^7$ | NEGATIVE |

Once the viremia was confirmed, they were applied with the avian derived concentrated formulation of the invention treatment. A 3 mL dose was intramuscularly applied. In order to assess the efficiency of the treatment, the clinical data were observed and the amount of circulating virus in the porcins was quantified.

The monitoring results after 10 days of the application of the avian derived concentrated IgY immunoglobulins formulation of the invention showed that 100% of the samples were negative to the presence of PRRS virus genetic material in serum.

With the obtained results, it is shown that an immunoglobulin schedule application in the broodstock prevents the viral circulation and may neutralize the viremia in weaning suckling pigs with loads of $10^7$ viral particles per mL.

Example 7

The Use of Concentrated IgY Immunoglobulines Reduces Suckling Pigs Mortality The avian derived concentrated IgY immunoglobulins formulation of the invention was applied to weaned and feedlot-aimed porcins. During all the production time, the mortality under different treatment systems was recorded.

The studied farm is located at the Midwest region of Mexico and has 1100 sow in its reproductive herd and a weekly production of 500 suckling pigs. The farm has antecedents of PRRS endemic infection, even when several control strategies have been deployed. There is an auto-replace system, which considers the introduction of sows every four months. The broodstock includes the application of the modified live virus vaccine against PRRS every three months.

In this example, a weekly monitoring was performed and the mortality percentage was calculated both in the weaning (weeks 3 to 9) and in the fattening period (week 10 to 26).

Two treatments were compared. One based in live vaccine and the other with the avian derived concentrated IgY immunoglobulins formulation of the invention, further, a naive control block was also considered. Each treatment was comprised by different groups which were independently assessed; groups 01 to 06 correspond to conventionally treated suckling pigs (live vaccine) and groups 07 to 16 were those that received two doses of the avian derived concentrated IgY immunoglobulins formulation of the invention, while groups 17, 18 and 19 were not treated.

| Treatment type | Treatment descriptions | Groups that received treatment |
|---|---|---|
| Modified live virus vaccine | Vaccine application at 21 days of age and 3 months. | 6, from 01 to 06 |
| PRRS-specific avian derived highly concentrated immunoglobulines (IgY type) | Two 3 ml each applications, week 1 and 10 after weaning. | 10, from 07 to 16 |
| Naive control | No treatment | 3, from 17 to 19 |

FIG. 5 shows the mortality monitoring starting on week 3 and until week 26. The groups treated with the avian derived concentrated IgY immunogloblins formulation of the invention are highlighted in a more intense blue box (groups 07 to 16).

The percentage of mean mortality of the naive groups was the highest one (25.06), followed by the groups that received the conventional treatment (average of 21.2%) and the best treatment was the one of the avian derived concentrated IgY immunoglobulins formulation of our invention, where a mean mortality percentage of 10.27% was obtained. This means, using the IgY immunoglobulins of the invention, a survival of almost 90% of the animals treated is reached, which represents 10% of that reached by the vaccination method.

FIG. 6 shows a chart of the cumulative mortality percentages of each assessed group, wherein those which were treated with the avian derived concentrated formulation of the invention are highlighted.

The results from the use of concentrated IgY type immunoglobulins show a relevant decrease in the mortality percentages associated to the PRRS virus. Moreover, it was noted that the health conditions and productivity of these animals was also improved, unlike the groups that received the vaccine. It is important to note that this is the first time that the use of avian immunoglobulins for the treatment of suckling pigs is proved.

These results are very relevant as the schedule comprising the avian derived concentrated IgY immunoglobulins formulation of the invention not only decreases the mortality percentage, but it also provides the possibility of obtaining other improvements in the productive parameters.

Thus, it will be appreciated that although the specific embodiments of the invention have been described here in for illustrative purposes, modifications may be made without departing from the nature and scope of the invention. Accordingly, the invention is not limited except by the appended claims.

The invention claimed is:

1. An emulsified vaccine formulation comprising: (i) antigens, (ii) MARCOL light mineral oil and (iii) chitosan, wherein the antigens have titers higher than 50% Embryo Infectious Dose ($EID_{50}$) $10^4$/ml and are one or more different strains of one or more Porcine Reproductive and Respiratory Syndrome (PRRS) viruses, and wherein the one or more PRRS viruses have an ORF5 gene nucleotide sequence selected from the group consisting of SEQ ID NO: 1, SEQ ID NO: 2, SEQ ID NO: 3, SEQ ID NO: 4, SEQ ID NO: 5, SEQ ID NO: 6 and SEQ ID NO: 7.

2. A process for immunoglobulins extraction, delipidation and concentration from egg yolks from hens hyperimmunized with the emulsified vaccine formulation of claim 1, wherein the process comprises the following steps:
    a) diluting the egg yolks 1:4 or 1:8 with 0.01% sodium azide and storing the egg yolks under refrigeration for at least 24 hours to allow formation of a supernatant;
    b) removing the supernatant and adding hydroxypropyl methylcellulose phthalate (HPMCP) to the supernatant at 1-15% in a 0.25 ml per each 100 ml of yolk ratio, and allowing the supernatant to rest for at least 24 hours to form a lipid layer and an aqueous part;
    c) separating the lipid layer from the aqueous part and filtering the aqueous part;
    d) adding PEG in a 5-30% weight/volume (W/V) ratio, mixing, and allowing to rest for at least 4 to 12 hours at 4° C.;
    e) centrifuging for 20 to 30 minutes to form a supernatant and a pellet, and removing the supernatant; and
    f) solubilizing the pellet with PBS 1× or TRIS buffer, at a volume equivalent to 10% of the original volume.

3. The process of claim 2, wherein the egg yolks diluted 1:4 or 1:8 with 0.01% sodium azide in step (a), are stored under refrigeration for 12 to 24 hours.

4. The process of claim 2, wherein in step (d), PEG8000 is added in a 5 to 30% W/V ratio, mixed and allowed to rest for at least 4 to 12 hours at 4° C.

* * * * *

SEQUENCE LISTING

```
<160> NUMBER OF SEQ ID NOS: 7

<210> SEQ ID NO 1
<211> LENGTH: 603
<212> TYPE: DNA
<213> ORGANISM: Porcine reproductive and respiratory syndrome virus
```

<400> SEQUENCE: 1

```
atgttgggga aatgcttgac cgcgggctgt tgctcgcagt tgcttttttt gtggtgtatc      60
gtgccgttct gttttgttgt gcccaccagc gccaacaaca gcagcagctc ccatttacag     120
ttgatttata acctgacaat atgtgagctg aatggcacag attggctaaa tgacaaattt     180
gattgggcag tggagacctt tgtcatcttt cctttattga ctcacattgt ctcctatggt     240
gccctcacca ccagtcactt ccttgacaca gccggtttga tcactgtgtc caccgccgga     300
tactaccacg gcggcatgt cctgagtagc atttacgctg tctgcgctct ggccgcgctg      360
atttgcttcg tcatcagact gacaaaaaac tgcatgtcct ggcgctactc atgtactaga     420
tatactaatt ttcttctaga caccaagggc aaactctatc gttggcggtc tcccgtcatt     480
atagagaaag ggggaaaaat cgaggttaac ggtcacttga tcgacctcaa gagagttgtg     540
cttgatggtt ccgcagcaac ccctgtaacc aaagtttcag cggaacaatg ggacgtcct     600
tag                                                                   603
```

<210> SEQ ID NO 2
<211> LENGTH: 603
<212> TYPE: DNA
<213> ORGANISM: Porcine reproductive and respiratory syndrome virus

<400> SEQUENCE: 2

```
atgttgggga aattcttgtc cgcgggctgt tgctcgcagt tgcttttttt gtggtgtatc      60
gtgccgttct gttttgttgc gcccaccaac gccaacaaca gcagcagctc ccatttacag     120
tcgatttata acctgacaat atgtgagctg aatggcacag attggctaga taaaaagttt     180
gattgggcag tggagacctt tgtcatcttt cctgtattga ctcacattgt ctcctatggt     240
gccctcacca ccagccattt ccttgacaca gtcggtttga tcactgtgtc caccgccgga     300
tactaccaca ggcggtatgt cctgagtagc atttacgctg tctgcgccct ggccgcgctg     360
atttgcttcg ccatcaggct gacaaaaaac tgcatgtcct ggcgctactc atgtactaga     420
tatactaatt ttcttctaga caccaagggc aaactctatc gttggcggtc tcccgtcatt     480
atagagaaag ggggaaaaat cgaggttaac ggtcacttga tcgacctcaa gaaagttgtg     540
cttgatggtt ccgcagcaac ccctgtaacc aaagtttcag cggaacaatg ggtcgtcct     600
tag                                                                   603
```

<210> SEQ ID NO 3
<211> LENGTH: 603
<212> TYPE: DNA
<213> ORGANISM: Porcine reproductive and respiratory syndrome virus

<400> SEQUENCE: 3

```
atgttgggga aatgcttgac cgcgggctgt tgctcgcaat tgcttttttt gtggtgtaac      60
gggccggtct gttttgttgg cccacccaac ggcagcaaca gcagcaggtt ccatttacag     120
ttgatttata acctgacaat atgtgagctg aatggcacag attggctaaa tgaacatttt     180
gattgggcag tggagacctt tgtcatcttc cctgtgttaa ctcacatcgt ctcctatggt     240
gccctcacca ccagtcattt ccttgacaca gtcggtttga tcactgtgtc caccgccgga     300
tactaccacg gcggtacgt cctgagtagc atttacgctg tctgcgccct ggccgcgctg      360
atttgcttcg ccatcaggtt aacaaaaaac tgcatgtcct ggcgctactc atgtactaga     420
tacactaatt ttcttctaga caccaagggt aaactctatc gttggcggtc tcccgtcatt     480
atagagaaag ggggaaaaat cgaggttaac ggtcacttga tcgacctcaa gaaagtcgtg     540
```
cttgatggtt ccgcagcaac ccctgtaacc aaagtttcag cggaacaatg gggtcgtcct    600
tag                                                                  603

<210> SEQ ID NO 4
<211> LENGTH: 603
<212> TYPE: DNA
<213> ORGANISM: Porcine reproductive and respiratory syndrome virus

<400> SEQUENCE: 4
atgttgggga aattcttgtc cgcgggctgt tgctcgcagt tgcttttttt gtggtgtatc     60
gtgccgttct gttttgttgc gcccaccaac gccaacaaca gcagcagctc ccatttacag    120
tcgatttata acctgacaat atgtgagctg aatggcacag attggctaga taaaaagttt    180
gattgggcag tggagacctt tgtcatcttt cctgtattga ctcacattgt ctcctatggt    240
gccctcacca ccagccattt ccttgacaca gtcggtttga tcactgtgtc caccgccgga    300
tactaccaca gcggtatgt cctgagtagc atttacgctg tctgcgccct ggccgcgctg    360
atttgcttcg ccatcaggct gacaaaaaac tgcatgtcct ggcgctactc atgtactaga    420
tatactaatt ttcttctaga caccaagggc aaactctatc gttggcggtc tcccgtcatt    480
atagagaaag ggggaaaaat cgaggttaac ggtcacttga tcgacactca agaaagttgt    540
gcttgatgtt ccgcagcaac ccctgtaacc aaagtttcag cggaacaatg gggtcgtcct    600
tag                                                                  603

<210> SEQ ID NO 5
<211> LENGTH: 603
<212> TYPE: DNA
<213> ORGANISM: Porcine reproductive and respiratory syndrome virus

<400> SEQUENCE: 5
atgttgggga aattcttgtc cgcgggctgt tgctcgcagt tgcttttttt gtggtgtatc     60
gtgccgttct gttttgttgc gcccaccaac gccaacaaca gcagcagctc ccatttacag    120
tcgatttata acctgacaat atgtgagctg aatggcacag attggctaga taaaaagttt    180
gattgggcag tggagacctt tgtcatcttt cctgtattga ctcacattgt ctcctaaggg    240
gccctcacca ccagccattt ccttgacaca gtcggtttga tcactgtgtc caccgccgga    300
tactaccaca gcggtatgt cctgagtagc atttacgctg tctgcgccct ggccgcgctg    360
atttgcttcg ccatcaggct gacaaaaaac tgcatgtcct ggcgctactc atgtactaga    420
tatactaatt ttcttctaga caccaagggc aaactctatc gttggcggtc tcccgtcatt    480
atagagaaag ggggaaaaat cgaggttaac ggtcacttga tcgacactca agaaagttgt    540
gcttgatgtg ccgcagcaac ccctgtaacc aaagtttcag cggaacaatg gggtcgtcct    600
tag                                                                  603

<210> SEQ ID NO 6
<211> LENGTH: 603
<212> TYPE: DNA
<213> ORGANISM: Porcine reproductive and respiratory syndrome virus

<400> SEQUENCE: 6
atgttgggga aatgcttgac cgcgggctgt tgctcgcgat tgctttcttt gtggtgtatc     60
gtgccgttct ggtttgctgc gctcgccaac gccaacagca ccggcagctc ccatctacag    120
ctgatttaca acttgacgtt atgtgagctg aatggcacag attggctaaa caacaatttt    180
aattgggcgg tggagagttt tgtcatcttt cccgttttga cccatattgt ctcctatggt    240

```
gccctcacca ccagccattt ccttgacaca gtcgctttag tcactgtgtc taccgccggg      300
tttgttcacg ggcggtatgt cctgagtagc atttacgcag tttgtgccct ggctgcgttg      360
atttgcttcg ttattaggtt tgtgaagaac tgcatgtcct ggcgctactc ttgtaccaga      420
tataccaact ttcttttaga caccaagggc aggctctacc ggtggcggtc acccgtcatc      480
atagaaaaga aaggtaaagt cgaggtcgac ggccacctga tcgacccaa gagagttgtg       540 cttgatggtc ccgcagcaac ccctgtaacc aaagtttcag cggaacaatg gggtcgtcct      600
tag                                                                    603

<210> SEQ ID NO 7
<211> LENGTH: 569
<212> TYPE: DNA
<213> ORGANISM: Porcine reproductive and respiratory syndrome virus

<400> SEQUENCE: 7
atgttgggga aattcttgtc cgcgggctgt tgctcgcagt tgcttttttt gtggtgtatc       60
gtgccgttct gttttgttgc gcccaccaac gccaacaaca gcagcagctc ccatttacag      120
tcgatttata acctgtggac aatatgtgag ctgaatggca cagattggct agataaaaag      180
tttgattggg cagtggagac ctttgtcatc tttcctgtat tgactcacat tgtctcctat      240
ggggccctca ccaccagcca tttccttgac acagtcggtt tgatcactgt gtccaccgcc      300
ggatactacc acaggcggta tgtcctgagt agcatttacg ctgtctgcgc cctggccgcg      360
ctgatttgct tcgccatcag gctgacaaaa aactgcatgt cctggcgcta ctcatgtact      420
agatatacta attttcttct agacaccaag ggcaaactct atcgttggcg gtctcccggc      480
attatagaga aaggggggaa aaatccaggt taacggtcac ttggatcgac ctcaagaaaa      540
atgtgcttga aggttccgca gcaacccc                                         569
```